United States Patent [19]

Waugh

[11] Patent Number: 4,802,441

[45] Date of Patent: Feb. 7, 1989

[54] DOUBLE WALL FAST COOL-DOWN FURNACE

[75] Inventor: Arthur Waugh, Winchester, Mass.

[73] Assignee: BTU Engineering Corporation, North Billerica, Mass.

[21] Appl. No.: 1,444

[22] Filed: Jan. 8, 1987

[51] Int. Cl.[4] ............................................. C23C 16/00
[52] U.S. Cl. .................................................... 118/666
[58] Field of Search ...................... 118/724, 725, 666; 219/385, 402

[56] References Cited

FOREIGN PATENT DOCUMENTS 57-153995 9/1982 Japan .

Primary Examiner—Richard Bueker

Attorney, Agent, or Firm—Weingarten, Schurgin, Gagnebin & Hayes

[57] ABSTRACT

One fast cool-down furnace embodiment discloses a double wall in the interspace of which a cooling air stream is flowable to provide fast cool-down of a load of wafers. The double wall embodiment is retrofittable on existing diffusion furnaces, and includes a cylindrical member aligned in concentric relation with the diffusion tube by combination plenum defining and supporting manifolds. In a second embodiment, the fast cool-down furnace includes a reaction vessel and a heating core relatively movable relative to each other in such a way that in a fast cool-down condition the core and reaction vessel are spaced apart. Cooling tubes are embedded in the movable core. Fans or other aids to cooling are provided. Operation is either in a controlled cool-down mode or in a quick quench mode.

7 Claims, 9 Drawing Sheets

DOUBLE WALL FAST COOL-DOWN FURNACE

CROSS REFERENCE TO RELATED APPLICATIONS

This invention is related to copending and commonly assigned U.S. utility patent application Ser. No. 001,445, now U.S. Pat. No. 4,753,192, entitled MOVEABLE CORE FAST COOL-DOWN FURNACE filed on even date herewith and invented by Forest S. Goldsmith, et al, incorporated herein by reference.

FIELD OF THE INVENTION

This invention is directed to the field of semiconductor processing furnaces, and more particularly, to a fast cool-down semiconductor furnace.

BACKGROUND OF THE INVENTION

Integrated circuits are typically manufactured on semiconductor material. In the common case, the semiconductor material is in the form of silicon wafers. The integrated circuits are formed on the wafers by one or more processing steps that are well known to those skilled in the art.

In some high-temperature processes, the wafers cannot be exposed to the atmosphere before they have cooled to an appropriately low temperature level. Exemplary are gate formation processes whereby plural wafers are introduced into semiconductor processing furnaces operating at around 1,000 degrees centigrade, and reactants in gas phase injected into the furnace selectively oxidize the semiconductor material. Thereafter, the wafers must be allowed to cool to approximately 600 degrees centigrade before being removed from the furnace and exposed to the atmosphere. Another exemplary process is the annealing of a titanium layer to form titanium disilicide on semiconductor wafers, which requires cooling from about 800 degrees centigrade, the annealing temperature, to about 150 degrees centigrade, the temperature at and below which the titanium disilicide coated wafers can be exposed to the atmosphere for handling. While the wafers are cooling, the utilization of the furnace is interrupted for an undesireably lengthy period, sometimes amounting to whole work shifts, so that the heretofore known semiconductor diffusion furnaces, in all such cases, suffer substantial production interruption, and revenue reductions.

SUMMARY OF THE INVENTION

The present invention contemplates as one object the provision of a semiconductor processing furnace capable of cooling down at a rate that is accellerated with respect to the rate at which the furnace would otherwise cool, so that the time interval required to cool to a preselected temperature is thereby materially reduced.

The present invention further comtemplates as another object a semiconductor processing furnace in which the rate is setable at which the temperature in the reaction zone is decreased, so that the wafers are exposed to a controlled rate of change of temperature.

The fast cool-down furnace of the present invention accomplishes these and other objects, and discloses in one presently preferred embodiment a cylindrical diffusion tube having a first diameter and defining a reaction chamber around which a cylinder of refractery material having an inside diameter greater than the outside diameter of the diffusion tube is concentrically mounted and in such a way as to provide an annular void therebetween. Manifolds respectively defining an air injection and an air removal plenum are mounted at the respective ends of the several cylinders for both supporting and aligning the cylinders in coaxial relation. An air circulation system including conduits, connected between the air injection and air removal manifolds and a fan, moves a cooling air stream through the input conduit, and into the input plenum. The input plenum distributes the cooling air into the annular void and longitudinally along the reaction chamber wall. The stream thereafter flows into the gas removal plenum, from whence it is exhausted to ambient out of the output conduit. The quantity and rate of gas flow along the cooling circuit is selectable to provide an intended rate of cool-down.

In another embodiment, the fast cool down furnace includes a furnace core that is mounted for sliding motion along an axis parallel to the axis of elongation of the diffusion tube of the furnace, and in such a way as to move away from the reaction vessel of the semiconductor diffusion furnace to provide fast cool-down, and is stopped at a position remote from the diffusion tube. Cooling tubes, embedded in the movable core, are flooded with a cooling air stream to cool the core. Plural fans are positioned around the furnace in position to cool the reaction vessel in the condition where the core is moved away from the reaction vessel.

BRIEF DESCRIPTION OF THE DRAWINGS

These and other objects, advantages, and aspects of the instant invention will become apparent as the invention becomes better understood by referring to the following solely exemplary and non-limiting detailed description of the preferred embodiments thereof, and to the drawings, wherein.

DETAILED DESCRIPTION OF THE PREFERRED EMBODIMENTS

Figure 1:
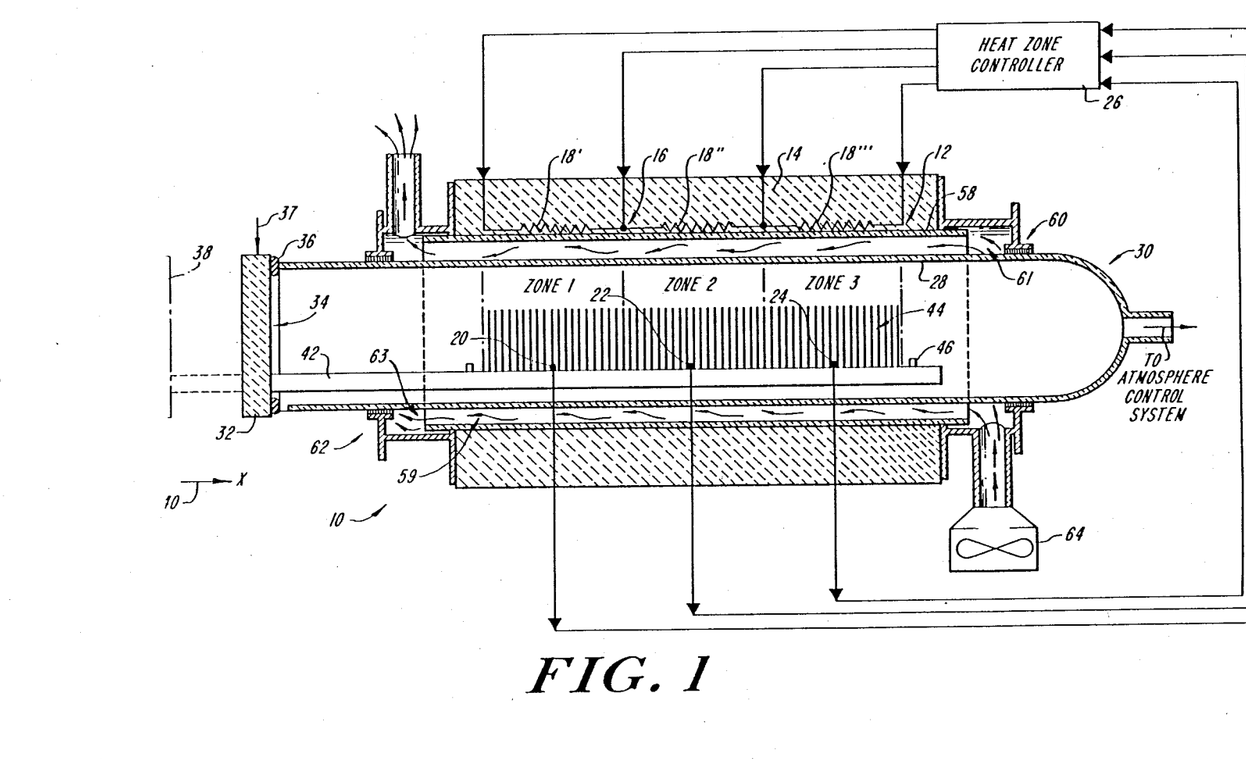
FIG. 1 is a partly pictorial, partly sectional view illustrating one embodiment of the fast cool-down furnace according to the present invention.

Referring now to FIG. 1, generally designated at 10 is a partially schematic partially pictorial diagram illustrating one embodiment of the fast cool-down furnace according to the present invention. As will become apparent as the invention becomes better understood, the furnace 10 is operable in one of a controlled mode and a quick quench mode. In the controlled mode, the rate of temperature change is selectable such that batches of wafers can cool at a selected rate of temperature change over one or several ranges of temperature. The rates selected in the one or more ranges can be the same or different. In the quick quench mode, the maximum rate of temperature change is realized, and the temperature of the batch of wafers is brought to below the temperature at which the wafers can be safely exposed to the atmosphere as quickly as is possible. In the quick quench mode the maximum temPerature change is achieved in the minimum time. The quick quench mode is thus particularly well suited for processes that require abrupt changes in temperature, as, for example, to induce a "freezing" of a desired microcrystalline structure.

The furnace 10 includes a core generally designated 12. The core 12 includes a matrix 14 of a high temperature insulating material. A hellically wound heating element generally designated schematically at 16 is embedded in the matrix 14 in well known manner. The core 12 may be the core of the so-called BDF-41 diffusion furnace commercially available from the assignee of the instant invention. The coil 16 preferrably includes three coil portions 18', 18", and 18''' so as to provide for three controlled temperature zones designated $Zone_1$, $Zone_2$ and $Zone_3$. Temperature sensors 20, 22, 24 respectively sense the temperature within the several zones. A heat zone controller 26 is operative to so energize the coil 16 that the zones have and maintain an intended temperature with respect to time characteristic. The sensors 20 may, for example, be thermocouples well known to those skilled in the art.

A reaction vessel 28 is slideably mounted with respect to the core 12. One end of the reaction vessel 28 has a tapering neck portion generally designated 30 which is connected to a vacuum or other atmospheric control system, not shown. The vacuum system may produce a sub-atmospheric pressure condition within the reaction vessel for exemplary vacuum chemical vapor deposition processes.

A door mechanism 32 is mounted to a mouth generally designated 34 of the reaction vessel 28 at the end thereof remote from the tapering neck 30. The door 32 is releasably sealed to the mouth 34 via, for example, O-rings 36. As illustrated schematically by an arrow 37, one or more reactant gases are injected in the reaction vessel via conduits provided therefor in the door 32.

A boat loading mechanism shown in dashed outline 38 is movable along an X direction indicated by an arrow 40. A cantilevered paddle 42 is mounted to the boat loading mechanism 38, and longitudinally extends through an opening provided therefor in the door 32 into the reaction vessel 28 longitudinally inwardly through the three zones thereof.

Wafers contained in boats schematically illustrated at 46 are removably positioned on the free-end of the cantilevered paddle 42. The boat loading mechanism 38 is operative to translate the furnace load of wafers along the X direction for loading the wafers into the reaction vessel for processing and for unloading the wafers out of the reaction vessel after processing. Reference may be had to commonly assigned U.S. Pat. No. 4,573,431 for its disclosure for an alternate reaction vessel that may be used in the place of the reaction vessel 28 having the tapering neck 28. Other boat loading mechanisms including boats-only loading, other door assemblies including those for the atmospheric and the vacuum processes, as well as other gas injection systems, are envisioned and are within the inventive system.

Figure 2:
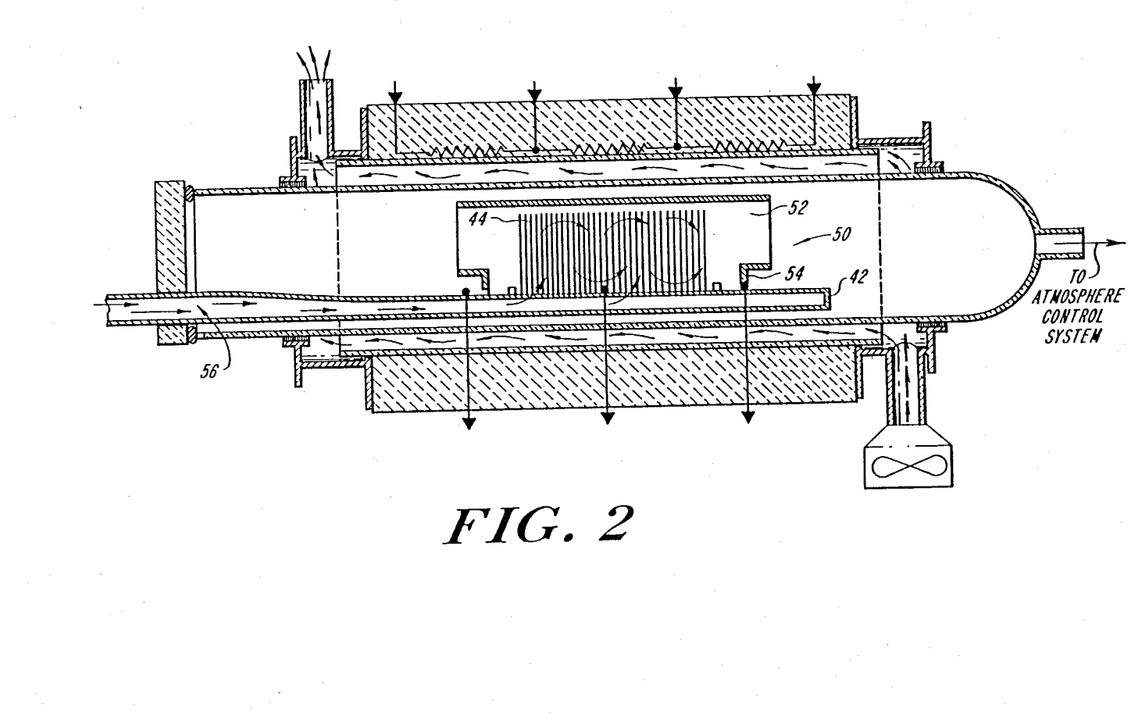
FIG. 2 is a partially pictorial, partially schematic view illustrating a modification of the FIG. 1 embodiment of the fast cool-down furnace according to the present invention.

In one modification shown in FIG. 2, for example, a cage generally designated 50 having mating and complimentary cage portions 52, 54 may be provided surrounding the batch of wafers 44 both before and after CVD and other processing. The cantilevered paddle 42 is provided with a conduit defining a gas flow passageway generally designated 56 in communication with the interior of the cage 50. Gas is controllably injected through the passageway 56 of the cantilevered paddle 42 and into the inside of the cage 50, where it circulates, as illustrated by the arrows. The injected gas typically is a purge gas, that both promotes cooling, as appears below, as well as provides a positive pressure inside the cage 50 which prevents backflow into the cage from the outside thereof, thereby both preventing contamination of the wafers by particulates as well as preventing exposure of the wafers to undesired gases. Other structures for providing protected and protective environments for the wafers during cool-down are contemplated.

Returning now to FIG. 1, an elongated cylinder of refractery material 58 having a diameter larger than that of the reaction vessel is provided concentrically surrounding the reaction vessel 28 and defines thereby a double-walled annulus generally designated 59, the inside wall of the surrounding cylinder of which and the confronting outside wall of the reaction vessel of which provide an annular fluid flow pathway that longitudinally extends along the length of the reaction zone of the reaction vessel at least along the three zones for both cooling the vessel and providing therefor a cold-wall.

Distribution and removal manifolds to be described generally designated 60, 62 are respeotively provided proximate the ends of the reaction vessel 28 and of the cylinder 58. The manifolds define a gas feed and a gas exhaust plenum 61, 63 in communication with the annular fluid flow pathway of the double walled annulus 59 for directing a cooling air stream into and along the vessel and for removing the air stream therefrom to exhaust. The manifolds 60, 62 coaxially support and align the reaction vessel 28 as well as the cylinder 58 in a manner to be described.

The members 60, 62 are retrofittable to already existing semiconductor diffusion furnaces, which thereby provides a fast cool-down capability in the controlled and quick quench modes for the existing furnaces at minimal costs. The members 60,62 also facilitate and ameliorate the burden of furnace service requirements. The removal and replacement of either the reaction vessel 26 or the cylindrical wall 58 is simply and readily accomplished by merely releasing the members 60, 62, from the core, slideably replacing the component to be replaced with a new or refurbished one, and re-fastening the members 60, 62 to the core. The members 60, 62 are sufficiently compact and self contained that plural cores 12 may readily be stacked to provide a vertical array of plural fast cool-down semiconductor processing furnaces each independently controllable to select the time-temperature characteristics suitable to the particular deposition or other process being run in the corresponding tube.

A fan or blower 64 is connected over a conduit to the distribution plenum 61 of the input manifold 60. The fan is operable to move a selected quantity of air at a selected rate into the plenum 61, which air is distributed thereby peripherally around the reaction vessel 28 as an annular stream longitudinally along the reaction vessel, and is received in the exhaust plenum 63 defined by the exhaust manifold 62. As the air is moved along the furnace, the heat in the reaction chamber of the furnace 5 is transported by conduction and radiative processes through the wall of the vessel 28 to the flowing air. The heat loss cools the inside of the reaction vessel, and concomitantly heats the flowing air in the passageway. The heated air is discharged out the exhaust manifold 62 to ambient or to a suitable gas reception system.

Figure 3:
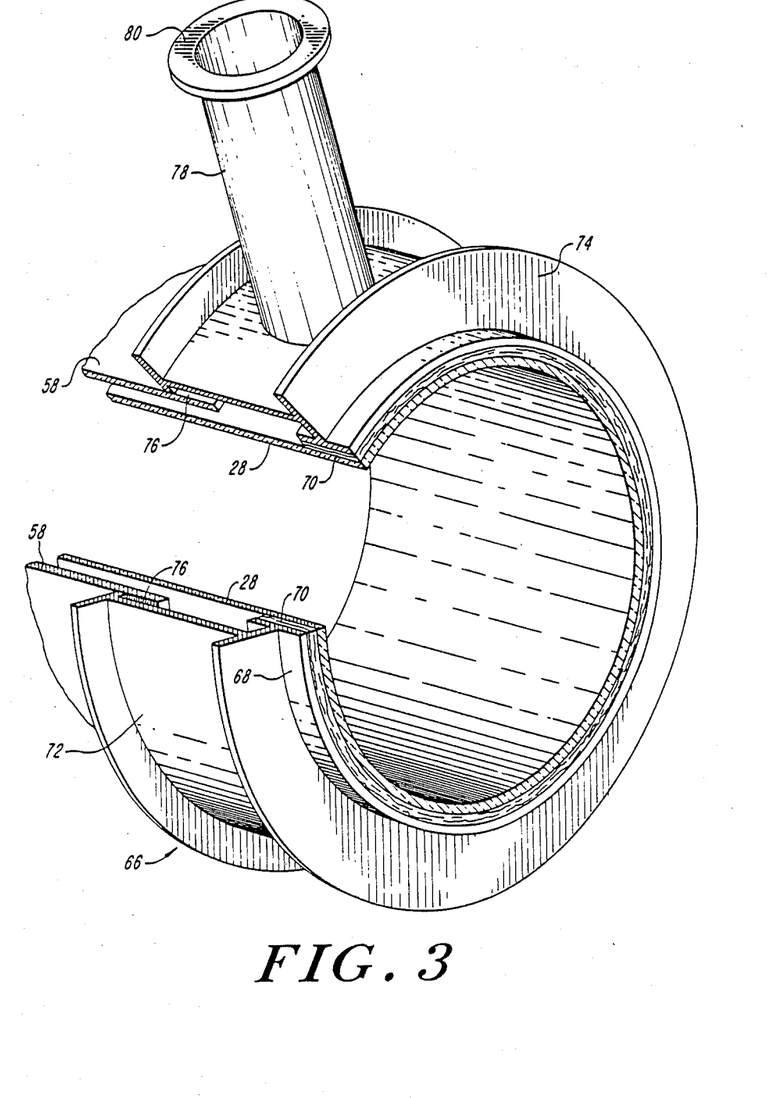
FIG. 3 is a perspective view illustrating a component of the FIGS. 1, 2 embodiments of the fast cool-down furnace according to the present invention.

Referring now to FIG. 3, generally designated at 66 is a perspective view illustrating a combination plenum providing and supporting manifold of the FIGS. 1, 2 embodiments of the fast cool-down furnace of the present invention. The input and exhaust manifolds are generally the same, except that they have reflective symmetry, and each includes a first annular rim 68 for supporting on its inside surface the outer surface of the reaction vessel. A sealing material 70 is provided between the inside surface of the annular support rim 68 and the outside surface of the reaction vessel. Any suitable sealing member may be employed such as a high temperature FIBER FRAXS paper.

An annular rim 72 of a diameter larger than the diameter of the rim 68 is concentrically mounted to the rim 68 by a sealing and strengthening web 74 welded perpendicularly to about the midpoint of the annular rim 68 and welded perpendicularly to the annular rim 72. The annular rim 72 supports with its inside surface the outside surface of the cylindrical member 58 (FIG. 1). An annular, high-temperature seal 76 is circumferentially provided between the confronting walls of the members 72, 58 (FIG. 1). Any suitable sealing material such as woven quartz or FIBER FRAX paper can be employed.

The region enclosed by the rims 68, 76 and the included wall 76, together with the proximate end of the thereby aligned and supported reaction vessel, define a distribution plenum and an exhaust plenum respectively at each of the ends of the fast cool-down furnace. A nipple 78 terminating on its free end in a strengthening flange 80 is welded or otherwise fastened to the annular rim 72. At the distribution plenum, input air is coupled thereinto through the corresponding nipple of the distribution manifold via a suitable coupling. The exhaust plenum is coupled to ambient via a conduit opening to atmosphere coupled to the nipple of the exhaust manifold. Any other suitable means for moving air from the distribution to the exhaust plenums such as a negative pressure source may be employed without departing from the inventive concept.

Figure 4:
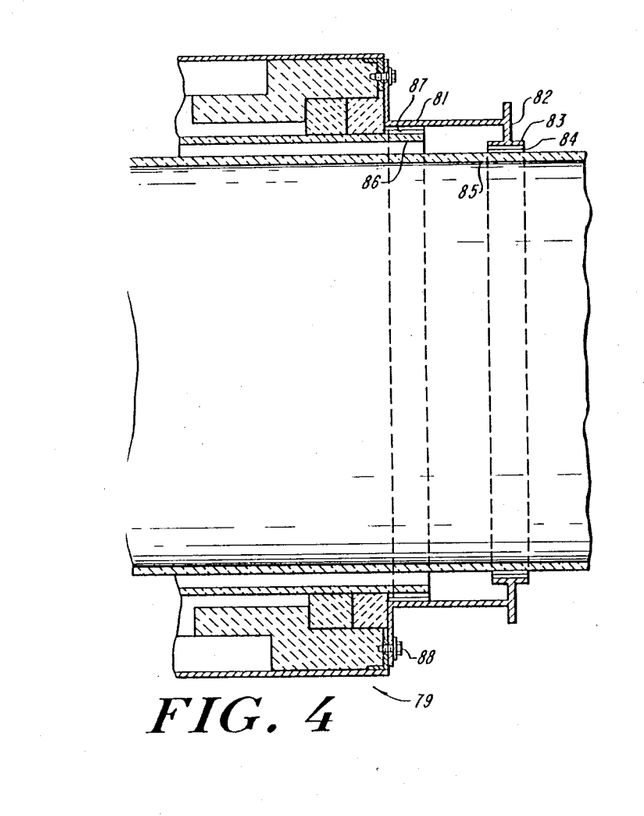
FIG. 4 is a detailed perspective view of a portion of the FIGS. 1, 2 embodiment of the fast cool-down furnace according to the present invention.

Referring now to FIG. 4, generally designated at 82 is a fragmentary perspective diagram illustrating the manner that the annular rims of the distribution and exhaust manifolds both support and align as well as define distribution plenums at the input and output ends of the fast cool-dwn furnace. The distribution plenum is specifically illustrated and is enclosed by the walls constituting annulus 81, web 82, annulus 83, seal 84, reaction vessel portion 85, cylindrical member portion 86 and seal 87. The air is thereby distributed peripherally around the reaction vessel 28 (FIG. 1) and is forced through an annular mouth that opens into the annular pathway defined by the double outer quartz cylindrical member and the inner quartz reaction vessel.

The supporting and plenum defining manifolds are comParatively simple to manufacture, and may be retrofit to the cores of existing furnaces to provide a fast cool-down furnace capability with a minimum capital expenditure. The conventional core, in accordance with the present invention, is readily modified by providing the manifolds at either end thereof, and in the illustrated embodiment, the manifolds are bolted to the core as at 88 (FIG. 4). For tube removal, or replacement, the bolts 88 need be only loosened from the core, which frees the manifolds. The manifolds may thus be slideably removed from the reaction vessel and the cylindrical wall member, and another reaction vessel or cylindrical wall member may e slideably inserted onto the core, and the same or a different manifold is slideably mounted over the ends thereof, which aligns the tubes, seals the plenums thereby created, and supports the coaxial cylindrical members.

Figure 5:
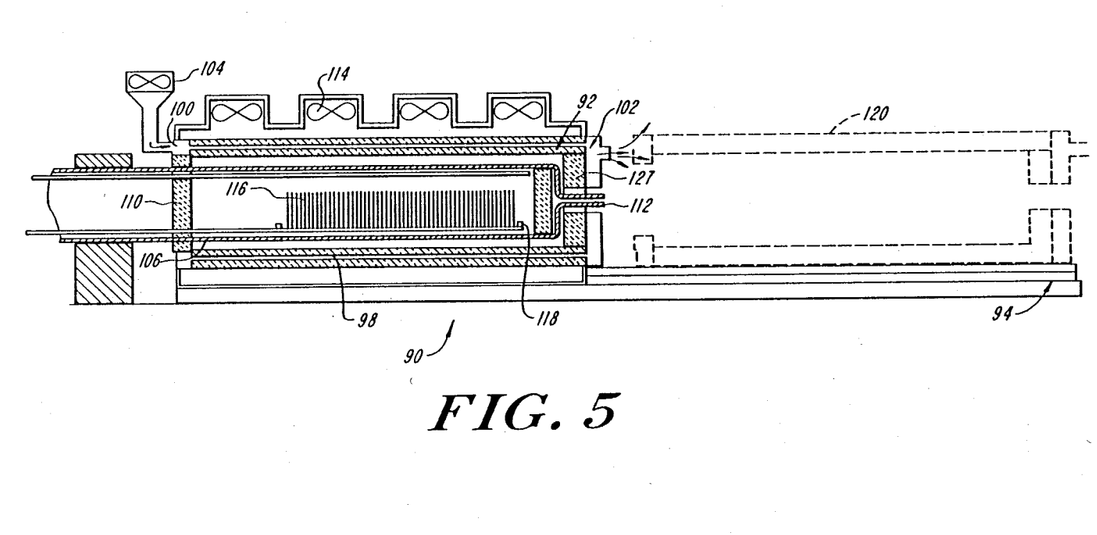
FIG. 5 is a partially pictorial, partially sectional diagram illustrating a second embodiment of the fast cool-down furnace according to the present invention.

Referring now to FIG. 5, generally designated at 90 is another embodiment of the fast cool-down furnace according to the present invention. The fast cool-down furnace 90 provides the fast cool-down action in such a way that the heating elements themselves of the furnace do not need to be turned off. The ability to maintain the heating elements energized while cooling the load of wafers is advantageous. The preheat retained by the coils materially reduces the heat-up time for the next cycle, substantially reduces overall energy usage, and, in a controlled ramp down mode, provides, in cooperation with the heat transport effected by embedded cooling tubes to be described, an intended degree of cool-down.

Figure 6:
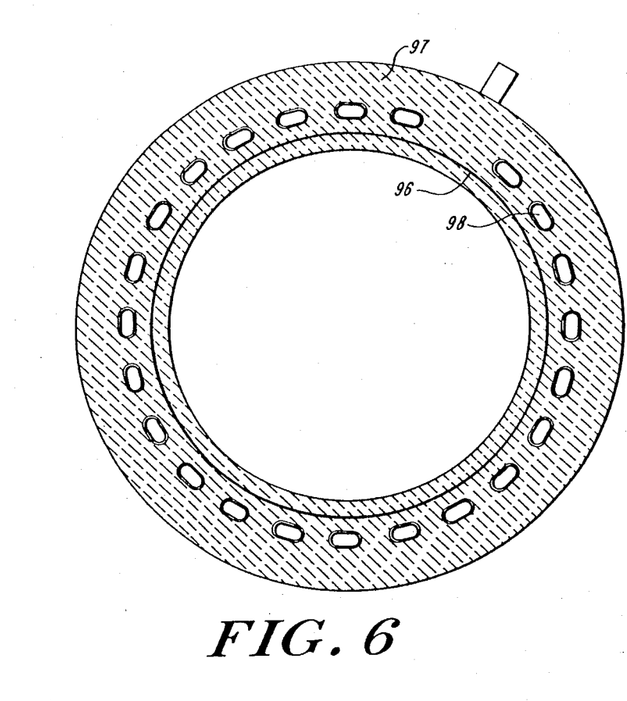
FIG. 6 is a sectional view of the core of the FIG. 5 embodiment of the fast cool-down furnace according to the present invention.

The furnace 90 includes a core generally designated 92 mounted for linear motion on a motor driven track 94. As illustrated in FIG. 6, the core 92 includes a helically wrapped resistance heating element 96 connected to a heater control, not shown, to provide controllable temperature zones along the length of the furnace core. The coil 96 is embedded in an insulative matrix 97. A plurality of elongated, flattened tubes 98 are embedded in the matrix 97 of the core in circumferentially symmetrically spaced relation therearound. The number and dimensions of the tubes is selected to provide an intended rate of core cool down.

Returning now to FIG. 5, manifolds generally designated 100, 102 are mounted to the ends of the core 12 and are coupled to the mouths of the several tubes 98. Air is moved through the tubes by a fan 104 coupled to the input manifold 100, and the discharged air is vented to ambient via the manifold 102.

A generally cylindrical reaction vessel 106 is supported in cantilevered fashion by a supporting tower 108. The cylindrical reaction vessel 106 is sealed at one end by an end closure 110 and at its other end it tapers to a neck 112 connectable to a vacuum system, not shown. Fans 114 are provided peripherally of the reaction vessel for directing cooling air onto the reaction vessel as described below.

In operation, a batch of wafers 116 to be processed, for example, in a high temperature gate oxidation step, are loaded into the reaction vessel 106 in boats 118 provided therefor. Two hundred and fifty four inch wafers can, for example, be easily accomodated. The end closure 110 is positioned to seal the mouth of the reaction vessel 106. The vacuum system, and the temperature control system, are activated. The fan 104, and the fans 114, at this time, remain in their inoperative condition, and the gate oxidation process is run. To quickly cool-down the wafers, the core 92 itself is slideably moved by the linear track 94 to a position remote from the reaction vessel 106, as illustrated in dashed outline 120. The fan 104 moves cooling air through the tubes of the core to reduce the heat emitted therefrom, while the heating elements of the core are kept at a predetermined level of energization. The fans 114 are operable to provide direct convective cooling of the reaction vessel 106 itself. After the wafers have cooled to below the temperature at which they may safely be handled in atmosphere, the end closure 110 is removed, the wafers 116 are slideably removed from the reaction vessel, and the same or another process is run on the same or another batch of wafers.

Figure 7:
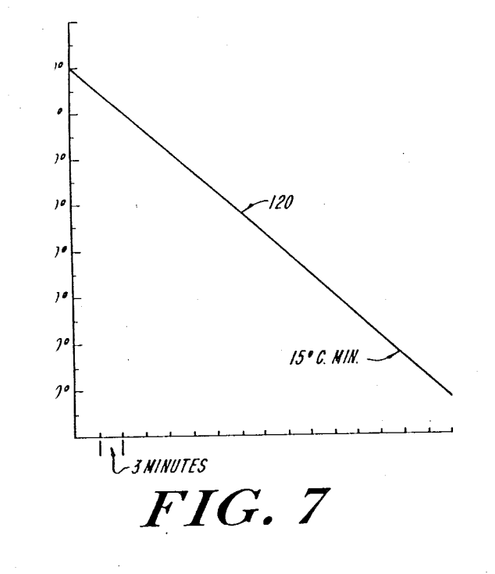
FIGS. 7 through 14 are graphs useful in explaining the operational performance of the several embodiments of the fast cool-down furnace according to the present invention.

Referring now to FIGS. 7 through 10, generally designated respectively at 120, 122, 124, and at 126 are graphs illustrating the temperature versus time performance of the FIGS. 1 through 4 embodiment of the fast cool-down furnace according to the present invention. The graph 120 in FIG. 7 shows a controlled 15 degree centigrade per minute ramp from 800 degrees. The load was 250 four inch wafers, was mounted on a section of a silicon carbide cantilevered paddle and was centered in the process tube. The thermocouples were located between the paddle and the load. With a 4800 cubic foot/hr. high volume low pressure cooling stream being applied, and with the tube closed with a one-half inch M-board, a substantially 15 degree centigrade per minute ramp was achieved to approximately 450 degrees centigrade.

Figure 8:
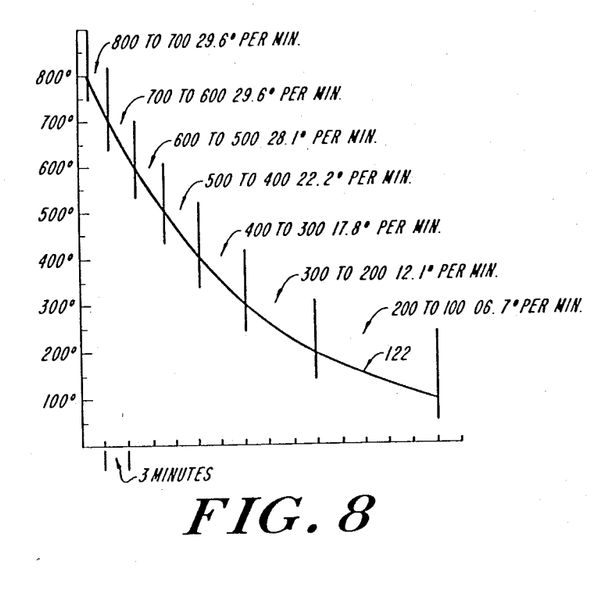

The curve 122 in FIG. 8 illustrates an uncontrolled cool-down from 800 degrees centigrade. Conditions were identical to the conditions that prevailed in FIG. 7, except that 20 liters per minute of $N_2$ was injected into the process tube, and no controlled cooling was effected. A rate of 30 degrees centigrade per minute was achieved from 800 degrees to 700 degrees and substantially 20 degrees centigrade per minute was achieved from 700 degrees to 200 degrees during operation in the uncontrolled quick-quench mode.

Figure 9:
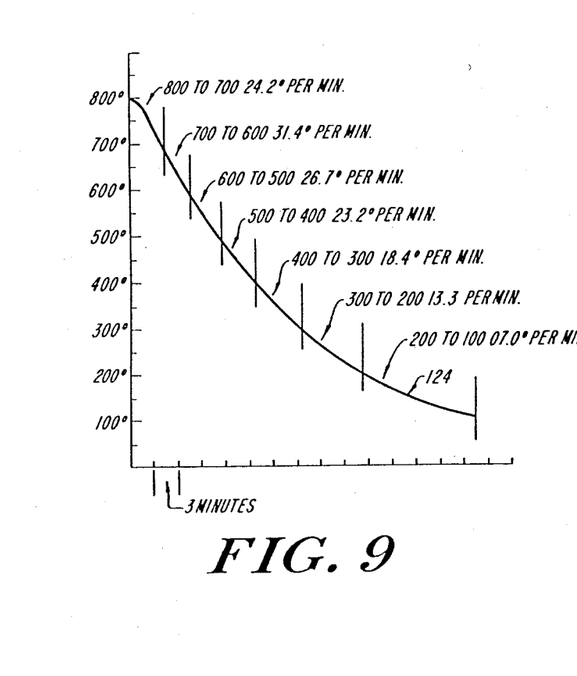

The curve 124 in FIG. 9 illustrates an uncontrolled cool-down from 800 degrees, but where the wafers were loaded on the floor of the reaction vessel, and the paddle itself was removed. The results simulate the conditions that would prevail in the reaction vessel in a wafer softlander system, such as that disclosed and claimed in commonly assigned copending U.S. utility patent application entitled "Wafer Soflanding System and Door Assembly", Ser. No. 784,836, incorporated herein by reference. The thermocouples were located on the boats in which the wafers were arrayed, and under the wafers. A rate of 25 degrees centigrade per minute was achieved between 800 and 700 degrees, and 21 degrees centigrade per minute cooling was achieved between 700 and 200 degrees, with no internal gas flow.

Figure 10:
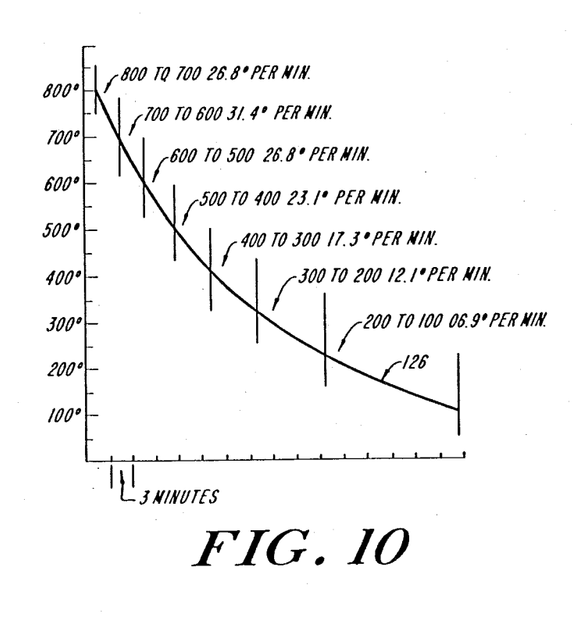
Figure 11:
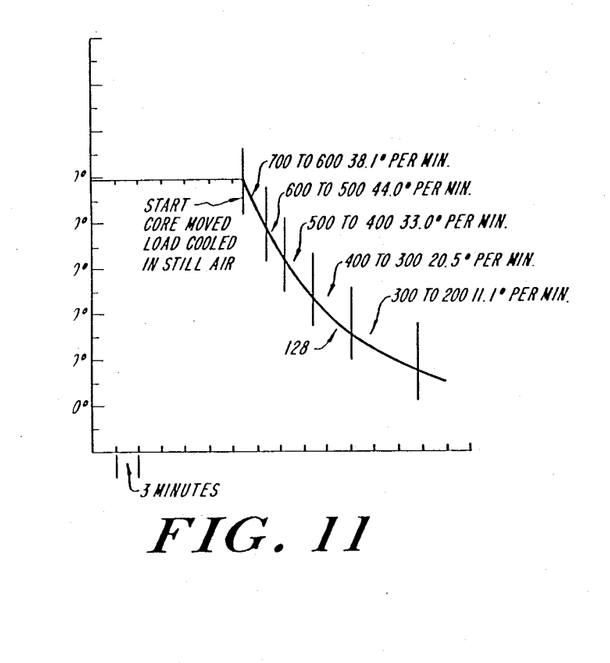

The curve 126 in FIG. 10 illustrates the temperature versus time characteristics of the simulated softlander system, but with an internal gas flow of 20 liters per minute of nitrogen injected into the process tube. A rate of 27 degrees centigrade per minute was achieved from 800 degrees to 700 degrees, and substantially 20 degrees centigrade from 700 degrees to 200 degrees centigrade.

Referring now to FIGS. 11 through 14, generally designated at 128, 130, 132, and 134 are graphs illustrating the operation of the FIGS. 5, 6 embodiment of the fast cool-down furnace of the present invention. Two hundred and fifty four inch wafers and boats were loaded in the reaction vessel, and thermocouples were located on the boats and under the wafers. A two inch brick end closure and a two inch brick radiation baffle were employed. The radiation baffle is designated at 127 in FIG. 5. The overall cooling rate between 700 and 200 degrees was approximately 24 degrees centigrade per minute in still air after the core had been moved away from the load.

Figure 12:
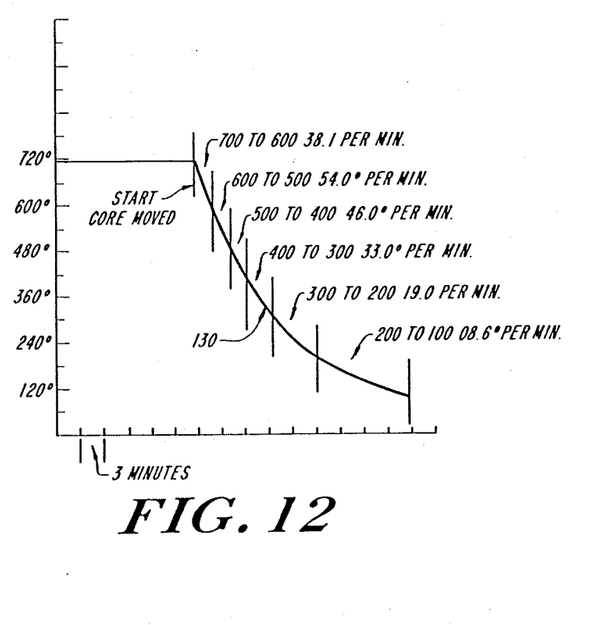

The graph 130 illustrates the temperature versus time performance when 4 "Tarzan" fans (designated 114 in FIG. 5), became operative for cooling the reaction vessel after the furnace core was moved. The four fans each had a three hundred forty cubic foot per minute rate. The overall cooling rate for the 700 degree to 200 degree range improved to approximately 33 degrees centigrade per minute.

Figure 13:
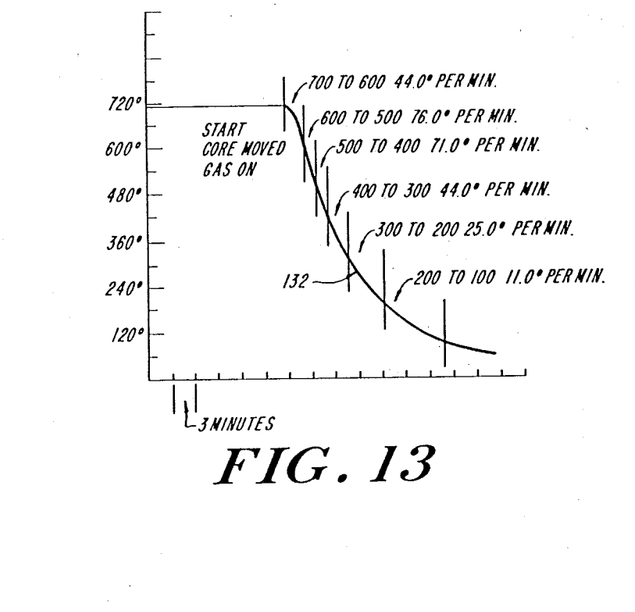

The curve 132 illustrates performance under the same conditions as those that prevailed in FIG. 12, but with an internal gas flow of 40 liters per minute $N_2$ injected into the process tube. The overall cooling rate was 44 degrees centigrade per minute in the 700 to 200 degree range.

Figure 14:
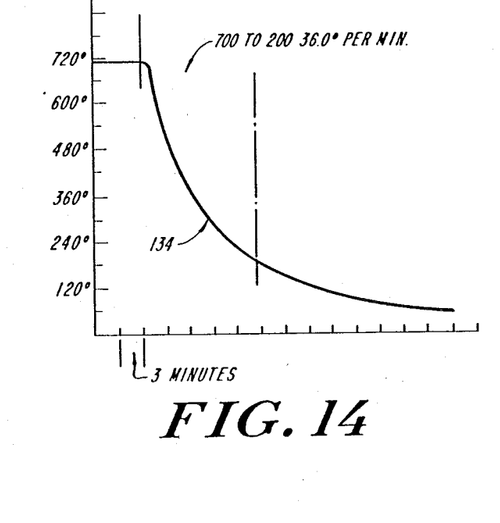

The graph 134 in FIG. 14 illustrates the effect on the temperature versus time characteristic by adding an additional "Tarzan" fan, five being employed rather than four as in the situation observed in FIG. 12. With five Tarzan fans, the overall cooling rate improved to approximately 36 degrees centigrade per minute.

The following table summarizes typical cooling periods for the several embodiments, as compared with a standard 10½ inch core.

|  | Typical cooling periods are: | | |
| --- | --- | --- | --- |
|  | 1000° to 700° | 700° to 200° | TOTAL |
| Double Wall Core | 11 min. | 25 min. | 36 min. |
| Moveable Core | 14 min. | 11 min. | 25 min. |
| Std. 10½" Core | 65 min. | 240 min. | 305 min. |

Many modifications of the presently disclosed invention including other methods and materials for providing inlet and exhaust manifolds will become apparent to those skilled in the art without departing from the inventive concept.

What is claimed is:
1. A fast cool-down furnace, comprising:
   a reaction vessel having an outer wall and defining an elongated reaction chamber having a length;
   means coupled to the reaction vessel for heating the reaction chamber;
   means coupled to the reaction vessel for injecting reactants in gas phase into the reaction chamber;
   means for providing an annular fluid flow passageway having an annular mouth and that is in concentric surrounding relation to and extends substantially along the length of the reaction chamber;
   means coupled to the annular fluid flow passageway for providing an annular duct in air-tight sealing relation to said mouth of said annular fluid flow passageway; and
   means coupled to said annular duct for moving an annular stream of fluid peripherally around the mouth and through the passageway for removing heat uniformly from around the reaction chamber.
2. The fast cool-down furnace of claim 1, further including means coupled to the reaction vessel for loading and removing wafers into and out of the reaction chamber.
3. The fast cool-down furnace of claim 1, wherein said annular passageway providing means includes an envelope having an inside wall that is larger in diameter than said reaction vessel and a manifold having concentric, radially spaced inner and outer annular rims interconnected by a web, the inner rim providing a sleeve into which the reaction vessel is slidably mounted, and the outer annular rim providing a sleeve into which the envelope is slidably mounted, the rims, the web, and the included regions of the reaction vessel and envelope defining said annular duct.

4. The fast cool-own furnace of claim 3, further including means connected to the duct for providing a fluid connection port to said duct.

5. The invention of claim 4, wherein said port providing means includes an annular nipple welded to said outer annular rim.

6. The fast cool-down furnace of claim 3, wherein the reaction vessel as well as the envelope are fabricated of a refractory material.

7. The fast cool-down furnace of claim 1, further including means for sensing the temperature in the reaction chamber, and further including means for controlling the heating means in response to the temperature sensed by the temperature sensing means to provide a selected rate of temperature change in the reaction chamber.

* * * * *